United States Patent
Morales

[19]

[11] Patent Number: 5,947,993
[45] Date of Patent: *Sep. 7, 1999

[54] STENT CRIMPING TOOL AND METHOD OF USE

[75] Inventor: Stephen A. Morales, Mountain View, Calif.

[73] Assignee: Advanced Cardiovascular Systems, Inc., Santa Clara, Calif.

[*] Notice: This patent is subject to a terminal disclaimer.

[21] Appl. No.: 09/157,064

[22] Filed: Sep. 18, 1998

Related U.S. Application Data

[63] Continuation of application No. 08/893,936, Jul. 15, 1997, Pat. No. 5,810,873.

[51] Int. Cl.⁶ .......................... A61M 29/00; A61B 17/00
[52] U.S. Cl. ................................. 606/198; 606/1
[58] Field of Search ................. 606/1, 108, 191, 606/192, 194, 195, 198, 200; 623/1, 12; 29/234, 235, 282, 283

[56] References Cited

U.S. PATENT DOCUMENTS

| | | |
|---|---|---|
| 696,289 | 3/1902 | Williams . |
| 4,468,224 | 8/1984 | Enzmann et al. . |
| 4,576,142 | 3/1986 | Schiff . |
| 4,644,936 | 2/1987 | Schiff . |
| 4,681,092 | 7/1987 | Cho et al. . |
| 4,697,573 | 10/1987 | Schiff . |
| 4,901,707 | 2/1990 | Schiff . |
| 4,907,336 | 3/1990 | Gianturco . |
| 5,132,066 | 7/1992 | Charlesworth et al. . |
| 5,133,732 | 7/1992 | Wiktor . |
| 5,183,085 | 2/1993 | Timmermans . |
| 5,189,786 | 3/1993 | Ishikawa et al. . |
| 5,437,083 | 8/1995 | Williams et al. . |
| 5,546,646 | 8/1996 | Williams et al. . |
| 5,626,604 | 5/1997 | Cottone, Jr. . |
| 5,630,830 | 5/1997 | Verbeek . |
| 5,653,691 | 8/1997 | Rupp et al. . |
| 5,738,674 | 4/1998 | Williams et al. . |
| 5,746,764 | 5/1998 | Green et al. . |
| 5,783,227 | 7/1998 | Dunham . |
| 5,785,715 | 7/1998 | Schatz . |
| 5,836,952 | 11/1998 | Davis et al. . |

FOREIGN PATENT DOCUMENTS

| | | |
|---|---|---|
| 159065 | 2/1921 | United Kingdom . |
| WO 98/14120 | 4/1998 | WIPO . |
| WO 98/19633 | 5/1998 | WIPO . |

*Primary Examiner*—Michael Buiz
*Assistant Examiner*—William Lewis
*Attorney, Agent, or Firm*—Fulwider Patton Lee & Utecht, LLP

[57] ABSTRACT

A device for enabling crimping of an intravascular stent onto a balloon catheter assembly. The stent crimping device includes a pair of elements, adapted to be held in the hands of the user, which enable one element, in which a stent and balloon catheter assembly are positioned to slidably move relative to the other element, and to move through a tapered opening to crimp the stent onto the balloon catheter assembly.

12 Claims, 2 Drawing Sheets

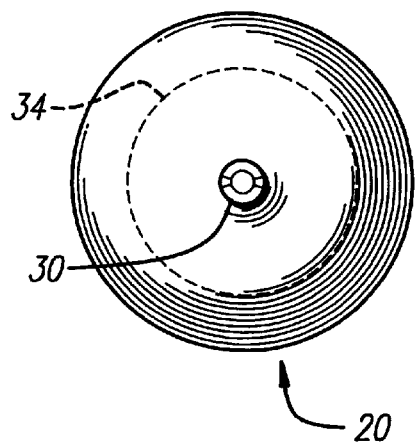
FIG. 4
FIG. 5
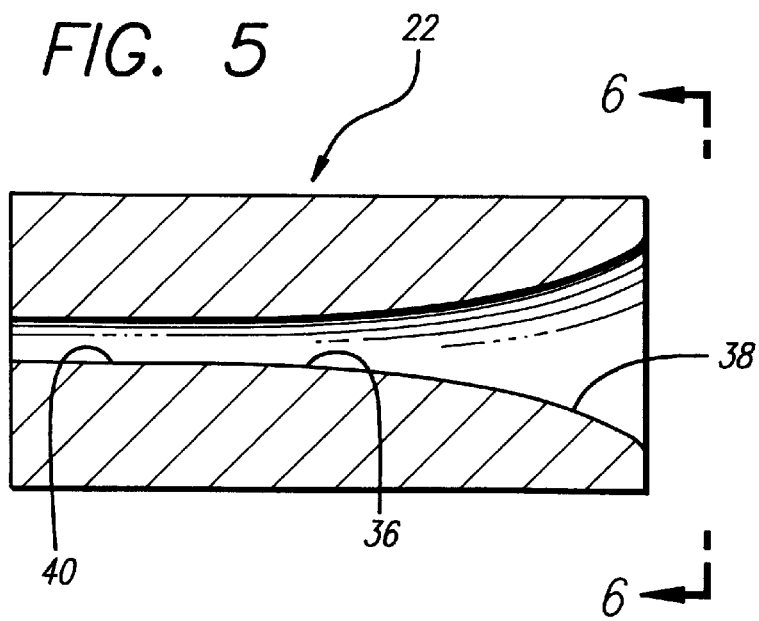
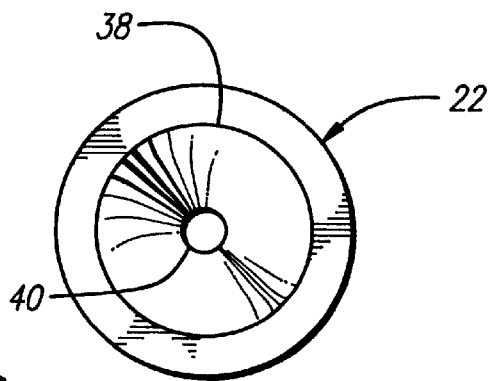
FIG. 6

STENT CRIMPING TOOL AND METHOD OF USE

This is a continuation application of parent application Ser. No. 08/893,936 filed Jul. 15, 1997, about to issue as U.S. Pat. No. 5,810,873 by the same inventor.

BACKGROUND OF THE INVENTION

1. Field of the Invention

The invention relates to a stent crimping device of the type that will enable the user to crimp a stent onto the distal end of a balloon catheter assembly, for example, of the kind used in a typical percutaneous transluminal coronary angioplasty (PTCA) or percutaneous transluminal angioplasty (PTA) procedure.

2. Description of the Related Art

In a typical PTCA procedure, for compressing lesion plaque against the artery wall to dilate the artery lumen, a guiding catheter is percutaneously introduced into the cardiovascular system of a patient through the brachial or femoral arteries and advanced through the vasculature until the distal end is in the ostium of the aorta. A guidewire and a dilatation catheter having a balloon on the distal end are introduced through the guiding catheter with the guidewire sliding within the dilatation catheter. The guidewire is first advanced out of the guiding catheter into the patient's coronary vasculature, and the dilatation catheter is advanced over the previously advanced guidewire until the dilatation balloon is properly positioned across the lesion. Once in position across the lesion, the balloon is inflated to a predetermined size with radiopaque liquid at relatively high pressures to radially compress the atherosclerotic plaque of the lesion against the inside of the artery wall and thereby dilate the lumen of the artery. The balloon is then deflated to a small profile, so that the dilatation catheter can be withdrawn from the patient's vasculature and blood flow resumed through the dilated artery. While this procedure is typical, it is not the only method used in angioplasty.

In angioplasty procedures of the kind referenced above, restenosis of the artery may develop over several months, which may require another angioplasty procedure, a surgical bypass operation, or some method of repairing or strengthening the area. To reduce the chance of the development of restenosis and strengthen the area, an intravascular prosthesis is implanted for maintaining vascular patency, typically called a stent. A stent is a device used to hold tissue in place in a vessel or to provide a support for a vessel to hold it open so that blood flows freely. A variety of devices are known in the art for use as stents, including balloon expandable tubular members, in a variety of patterns, that are able to be crimped onto a balloon catheter, and expanded after being positioned intraluminally on the balloon catheter, and that retain their expanded form. Typically, the stent is loaded and crimped onto the balloon portion of the catheter, and advanced to a location inside the artery after a PTCA or PTA procedure. The stent is then expanded to a larger diameter, by the balloon portion of the catheter, to implant the stent in the artery. Typical stents and delivery catheters are disclosed in U.S. Pat. Nos. 5,514,154 (Lau et al.), 5,569,295 (Lam) and 5,507,768 (Lau et al.), which are incorporated herein by reference.

However, if the stent is not tightly crimped onto the catheter balloon portion, when the catheter is advanced in the patient's vasculature the stent may move or even slide off the catheter balloon portion in the coronary artery prior to expansion, and may block the flow of blood, requiring procedures to remove the stent.

In procedures where the stent is placed over the balloon portion of the catheter, the stent must be crimped onto the balloon portion to prevent the stent from sliding off the catheter when the catheter is advanced in the patient's vasculature. In the past this crimping was often done by hand, which does not provide optimum results due to the uneven force being applied, resulting in non-uniform crimps. In addition, it was difficult to judge when a uniform and reliable crimp had been applied. Though some tools, similar to ordinary pliers, have been used to apply the stent, these tools have not been entirely adequate in achieving a uniform crimp. Moreover, an unevenly crimped stent may result in an unevenly expanded stent in the vessel or artery, which is undesirable.

The present invention solves the problems associated with the prior art devices and provides a crimping tool that tightly and uniformly crimps the stent on the balloon portion of the catheter.

SUMMARY OF THE INVENTION

The invention is directed to a stent crimping device which enables crimping of a stent onto a catheter balloon portion, to better secure the stent onto the catheter for delivery of the stent through the patient's vasculature.

In an exemplary embodiment of the present invention, the stent crimping device includes a pair of elements adapted to be held in the hands of the user, to enable the user to move one element relative to the other, and to slide the stent and balloon catheter assembly, connected to one element, through a restricted opening in the other element, through which the stent and balloon catheter assembly are slidably movable. The restricted opening applies compressive force on the stent and balloon catheter assembly, to crimp the stent onto the balloon catheter assembly.

The device enables the stent to be tightly and uniformly crimped onto the distal end of a balloon catheter, reducing the risk that the stent may slide off the catheter balloon portion.

These and other advantages of the invention will become more apparent from the following detailed description thereof when taken in conjunction with the accompanying drawings.

BRIEF DESCRIPTION OF THE DRAWINGS

FIG. 4 is an end elevational view of the element shown in FIG. 3, taken along line 4—4 of FIG. 3.

FIG. 5 is a side elevational sectional view of the element through which the stent and catheter balloon portion are slidably movable.

FIG. 6 is an end elevational view of the element shown in FIG. 5, taken along line 6—6 of FIG. 5.

DETAILED DESCRIPTION OF THE PREFERRED EMBODIMENTS

The stent crimping device of the present invention is designed to allow a catheter lab (cath lab) physician or personnel to crimp a stent onto the balloon portion of a catheter. The stent crimping device will allow cath lab personnel to crimp essentially any type of balloon-expandable stent onto any type of balloon catheter, such as a typical balloon dilatation catheter used in a PTCA or PTA procedure.

The stent crimping device is formed generally of two parts including a handle portion and a cylinder portion which are designed to be held in the user's hands for drawing the stent and balloon through the tapered cylinder portion to crimp the stent onto the balloon. The handle and cylindrical portion are depicted as having preferred shapes, however, as will be appreciated these shapes can be modified to suit specific cath lab requirements or to accommodate stent and balloon catheter assemblies having various dimensions.

Figure 1:
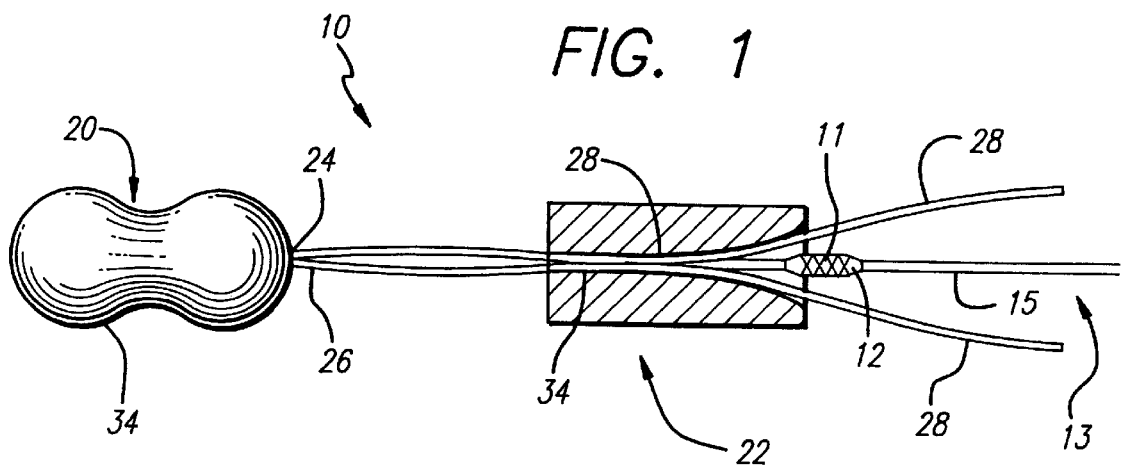
FIG. 1 is a partial sectional elevational view of an exemplary embodiment of the present invention, prior to slidably moving the stent and catheter balloon assembly through a restricted opening in an element.
Figure 2:
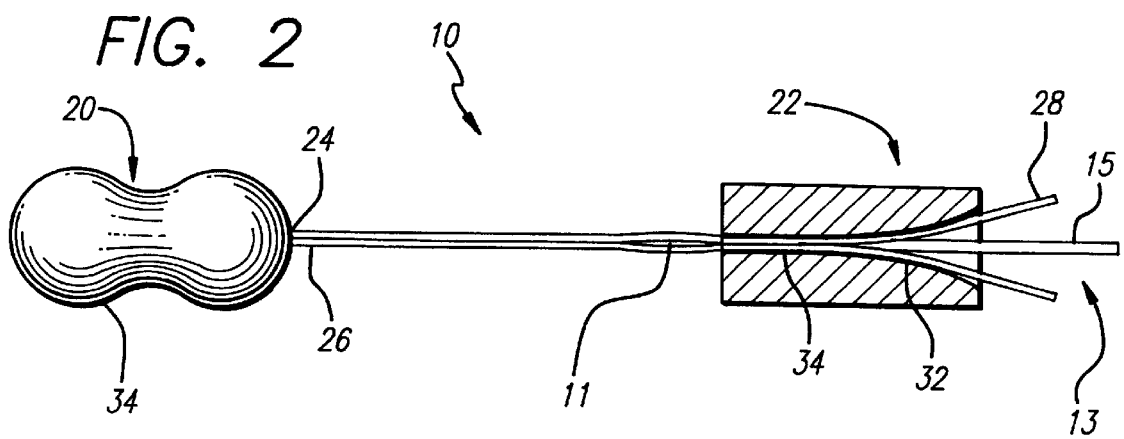
FIG. 2 is a view similar to FIG. 1 after the stent and catheter balloon portion have slidably moved through the restricted opening such that the stent is crimped onto the catheter balloon portion.

As can be seen in FIGS. 1 and 2, stent crimping tool 10 comprises handle element 20 and cylindrical element 22 for crimping an intravascular stent 11 onto the collapsed balloon portion 12 of a balloon catheter assembly 13. In the exemplary embodiment of tool 10, as shown in FIGS. 1–6, handle element 20 and cylindrical element 22 are adapted to be held in the hands of the user, so as to enable the user to slide stent 11 and balloon catheter portion 12 through the cylindrical element, to apply compressive force thereto to crimp the stent onto balloon portion of the catheter.

Figure 3:
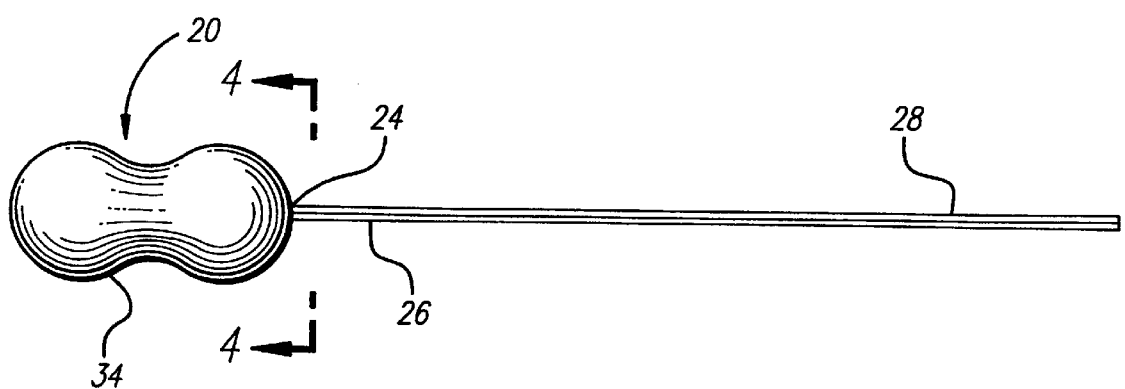
FIG. 3 is a side partial fragmentary elevational view of the element from which strands and the balloon catheter extend.

As shown in FIGS. 3 and 4, handle element 20 includes an opening 24 therein, in which first end 14 of catheter 15 is insertable so as to be releasably retained therein. First ends 26 of a plurality of thin elongated strands 28, comprised of flexible material, are secured in opening 24, and strands 28 extend therefrom so as to be extendable along and about catheter 15 and stent-loaded balloon catheter portion 12 thereof.

Opening 24 may have a diameter, for example, ranging from about 0.0500 to 0.2000 inch, with six sections 30 formed therein extending arcuately at 60° angles, for securing first ends 26 of elongated strands 28 therein. The elongate strands 28, having six sections 30, essentially form a cylindrical tube for receiving the stent and balloon prior to and during the crimping procedure. Depending upon the diameter of opening 24, it may be necessary to increase or decrease the number of sections 30, which may range from a single annular section up to perhaps twelve sections. Sections 30 are preferably arcuate-shaped, but can be flat or rectangular.

Handle element 20 further includes a reduced diameter gripping portion 34 for enabling the user to grip and pull elongate strands 28 through the cylindrical element.

Cylindrical element 22, as depicted in FIGS. 5 and 6, includes channel 36 extending therethrough. Catheter 15, stent-loaded balloon catheter portion 12 thereof, and strands 28 all are slidably-movable through channel 36. Channel 36 includes channel first portion 38 having a diameter greater than the diameter of stent-loaded balloon catheter portion 12 and strands 28, tapering to a reduced diameter substantially the same as the diameter of stent-loaded balloon catheter portion and strands 28. The diameter of channel first portion 38 may, for example, taper from a diameter of 0.250 inch to a diameter of 0.034 inch. Channel 36 includes channel second portion 40 having a diameter substantially the same as the diameter of stent-loaded balloon catheter portion and strands 28 after crimping stent 11 onto balloon catheter portion 12. For example, the diameter of channel second portion 40 may be a constant 0.034 inch. Since the diameter of channel second portion 40 defines the stent crimped diameter, the diameter can vary depending upon the application.

In the preferred method of crimping, the stent is loaded onto the deflated balloon portion of the catheter assembly. The elongate strands 28 are already positioned and extending through the cylindrical element and flared outwardly to receive balloon portion 12 and stent 11 of catheter assembly 13. The user then grips handle element 20 in one hand and cylindrical element 22 in the other hand and pulls the two assemblies in opposite directions so that the elongate strands 28 collapse onto the stent and balloon portion of the catheter assembly. Continued pulling of the assemblies in opposite directions results in the stent and balloon portion of the catheter assembly to be drawn through the continually narrowing taper formed in the second cylindrical element. The stent is gradually crimped onto the balloon portion of the catheter assembly as it is pulled through the taper and into and through channel second portion 40, the diameter of which substantially defines the crimped diameter of the stent with the thickness of the elongate strands around the stent. Continued pulling of the handle element in the opposite direction of the cylindrical element permits elongate strands 28 to be pulled clear of the second cylindrical element along with the now crimped stent. Thereafter, the stent and balloon portion of the catheter assembly can be carefully pulled back through the cylindrical element without the elongate strands, resulting in the stent being tightly crimped onto the balloon portion of the catheter.

The stent crimping tool 10 is designed to come either assembled or unassembled so that the cath lab personnel can choose the appropriate diameter of the channel second portion 40. The inner diameter of the channel second portion, in one preferred embodiment, may be about 0.034 inch. It will be appreciated, however, that this diameter can vary substantially depending upon the diameter of a deflated balloon, including the diameter or thickness of the stent when crimped onto the balloon, taken in conjunction with the diameter of the vessel which receives the implanted stent. Thus, for example, for a saphenous vein graft (SVG), the inner diameter of cylindrical element 22 may be much larger than 0.034 inch. As is clear, the resulting diameter of the stent as crimped onto the balloon is a matter of choice of the cath lab personnel to fit the particular application.

As can be appreciated, stent crimping tool 10 is designed for crimping stents having various diameters onto the balloon portion of a catheter. In order to more easily accommodate varying diameters of stents and to insure that the crimping process is smooth and results in a non-locking taper, the taper created by channel first portion 38 as it reduces in diameter to channel second portion 40, preferably angles in range of about 10° to 20° from the longitudinal axis of channel 36.

The stent crimping tool is designed for one-time use in a cath lab and it is intended to be destroyed after each use so that sterilization after use does not become a factor. The stent crimping device also can be used by stent and catheter manufacturers to crimp their stents onto catheters and package the assembly for sale to cath labs.

In one preferred embodiment, the handle element and the cylindrical element are formed from a rigid plastic which is capable of being machined into the specific dimensions for optimal performance. The inner diameter of cylindrical element 22 typically will be bored so that precise diameters can be achieved, since it will define the final crimped diameter of the stent. Moreover, it is important to provide a channel that is uniform and free of machining irregularities such as nicks or ridges. Thus, channel 40 preferably is bored or machined to provide precise diameters.

In order to facilitate drawing the elongate strands through the tapered bore or channel of the cylindrical element, a lubricous coating can be added to either elongate strands 28 channel 36 or both. The channel, which is a tapered bore, can have a lubricous coating which allows the flexible strands to more easily be pulled therethrough. Further, the elongate strands also can have a lubricous coating to ensure that they are easily pulled through the channel while crimping the stent onto the balloon portion of the catheter. Importantly, the elongate strands should be thin, flexible and compliant members, and be made from elastomeric materials, mylar, or the like.

While in the preferred embodiment the stent described is intended to be an intraluminal vascular prosthesis for use within a blood vessel, and the balloon delivery catheter is the same as or similar to that used in PTCA or PTA procedures, it will be appreciated by those skilled in the art that modifications may be made to the present invention to crimp any type of stent on any catheter. The present invention is not limited to stents that are deployed in a patient's vasculature, but has wide applications to crimping any type of graft, prosthesis, liner or similar structure. Furthermore, the stent may be delivered not only into coronary arteries, but into any body lumen. Other modifications can be made to the present invention by those skilled in the art without departing from the scope thereof.

What is claimed is:

1. A crimping tool assembly for crimping a stent onto a balloon catheter assembly, the crimping tool assembly, comprising:
    a handle having a first end and a second end;
    a plurality of flexible strands extending cantilevered from the second end of the handle, the plurality of strands flaring outward;
    a cylindrical element having a tapered smooth bore extending at least partially therethrough, the tapered bore having a small inner diameter at an end and a large diameter at an opposite end, wherein the plurality of flexible strands pass through the tapered bore.

2. The assembly of claim 1, wherein the plurality of flexible strands includes at least six strands.

3. The assembly of claim 1, wherein the small inner diameter includes a diameter of the stent when crimped onto the balloon catheter.

4. The assembly of claim 1, wherein the plurality of strands are located every 60 degrees about the circumference of the second end of the handle.

5. A crimping tool assembly for crimping an intravascular stent onto a balloon catheter assembly, the crimping tool assembly comprising:
    a handle having opposite ends;
    a plurality of thin, flexible strands extending from one end of the handle, the plurality of strands disposed to collectively form a hollow tube;
    a cylindrical element having a smooth bore, wherein the plurality of strands pass through the bore enabling slidable movement of the cylindrical element along the plurality of strands;
    wherein the bore is flared to include a small diameter at one end and a large diameter at an opposite end.

6. The assembly of claim 5, wherein the bore includes a section having a constant small diameter.

7. The assembly of claim 5, wherein the small diameter includes a diameter of the stent when crimped onto the balloon catheter.

8. The assembly of claim 5, wherein the bore includes lubricous coating.

9. The assembly of claim 5, wherein each strand includes an arcuate shape cross section.

10. A crimping tool assembly for crimping a stent onto a balloon catheter assembly, the crimping tool assembly, comprising:
    a rounded handle having a first end and a second end;
    a plurality of flexible strands extending cantilevered from the second end of the handle and disposed in a circular pattern;
    a cylindrical element having a tapered, smooth bore extending at least partially therethrough, the tapered bore having a small inner diameter at an end and a large diameter at an opposite end facing away from the handle, wherein the plurality of flexible strands pass through the tapered bore.

11. The assembly of claim 10, wherein the tapered bore includes a smooth, arcuate contour.

12. The assembly of claim 10, wherein the plurality of flexible strands include a lubricous coating.

* * * * *

UNITED STATES PATENT AND TRADEMARK OFFICE
CERTIFICATE OF CORRECTION

PATENT NO. : 5,947,993
DATED : September 7, 1999
INVENTOR(S) : Stephen A. Morales It is certified that error appears in the above-identified patent and that said Letters Patent is hereby corrected as shown below:

Title page, item [56], References Cited, after "FOREIGN PATENT
    DOCUMENTS" add, --OTHER PUBLICATIONS--, followed by
    --The eXTraordinary Stent, C.R. Bard Brochure, (undated).--.

Column 5, claim 1, line 34, after "tapered", add --,--.

Signed and Sealed this

Fourteenth Day of March, 2000

Attest:

Attesting Officer

Q. TODD DICKINSON

Commissioner of Patents and Trademarks